United States Patent [19]

Banko

[11] 4,253,199
[45] Mar. 3, 1981

[54] SURGICAL METHOD AND APPARATUS FOR IMPLANTS FOR THE EYE

[75] Inventor: Anton Banko, New York, N.Y.

[73] Assignee: Surgical Design Corporation, New York, N.Y.

[21] Appl. No.: 945,537

[22] Filed: Sep. 25, 1978

[51] Int. Cl.³ .......................... A61F 1/16; A61F 1/24
[52] U.S. Cl. ........................................................ 3/13
[58] Field of Search ......................................... 3/13, 1

[56] References Cited

U.S. PATENT DOCUMENTS

| | | | |
|---|---|---|---|
| 3,711,870 | 1/1973 | Deitrick | 3/13 |
| 3,961,379 | 6/1976 | Highgate | 3/13 |
| 4,073,015 | 2/1978 | Peyman et al. | 3/13 |
| 4,172,297 | 10/1979 | Schlegel | 3/13 |

FOREIGN PATENT DOCUMENTS 2313010  12/1976  France ............................................. 3/13

Primary Examiner—Ronald L. Frinks
Attorney, Agent, or Firm—Darby & Darby

[57] ABSTRACT

A method of removing a lens from the eye of a human and replacing said lens by an implant of deformable material to serve as a replacement lens in which the implant is attached to the ciliary body of the eye to be deformed thereby. Various forms of implants and implant capsules are also described.

22 Claims, 8 Drawing Figures

SURGICAL METHOD AND APPARATUS FOR IMPLANTS FOR THE EYE

The present invention relates generally to improvements in surgical procedures relating to the eye, and more particularly, to a method for removing the lens of the eye of a human and replacing the same by a substitute implant and to novel implants.

Several types of surgical procedures are used today for removing lenses from the eye which suffer from various types of defects, such as cataracts. The lens is removed, for example, by an ultrasonic procedure, in which it is emulsified, or by a mechanical cutting procedure which is described, for example, in my U.S. Pat. No. 3,996,935. That patent also describes a procedure for filling the eye capsule with fluid (liquid or gas) after the lens has been removed to serve as a substitute for the removed lens.

In another type of surgical procedure, once the lens has been removed, it is replaced by an implant which has an optical lens thereon, which can be made of either glass or a hard or a soft plastic. In this procedure the lens implant is not controlled by any of the eye muscles or tissue.

The present invention relates to a method and a device for overcoming the aforesaid disadvantages. More particularly, in accordance with the surgical method, the eye lens is removed together with the anterior portion of the lens capsule. In some cases, the posterior capsule is also removed together with the zonules which hold the lens capsule in the eye. After removal of the eye lens, it is replaced by an implant which, in accordance with a preferred embodiment of the invention, is formed of a suitable inert deformable or elastic material. The implant is attached to the eye by attaching it to the ciliary body. The implant can then deform in accordance with the muscle reflexes of the ciliary body and better perform a true, variable lens function.

It is therefore an object of the present invention to provide a surgical method and devices for use with the surgical method in which the lens of an eye is removed and replaced by an implant which is attached to the ciliary body of the eye.

A further object is to provide a method for operating in the eye and a device for use in the method comprising an implant made of a deformable plastic material which is attached to the ciliary body of the eye.

An additional object is to provide novel implants and implant capsules to replace a removed eye lens in which the implants are adapted to be attached to a portion of the eye.

Other objects and advantages of the present invention will become more apparent upon reference to the following specification and annexed drawings in which.

Figure 1:
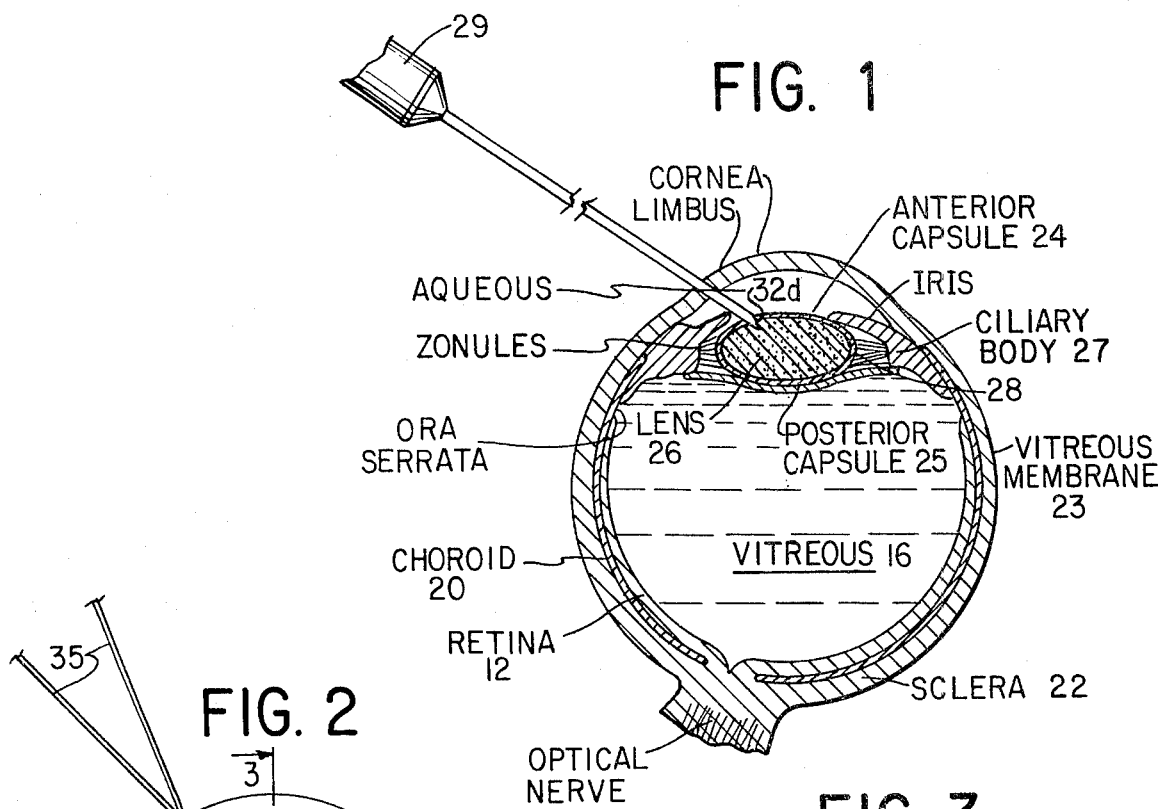
FIG. 1 is an elevational view in section showing a portion of the eye which is to be operated upon.

FIG. 1 is a cross-sectional view of the eye showing its various parts. The parts of interest here have been labeled and include a retina 12, surrounded by the choroid 20, which in turn is covered by the sclera 22. The vitreous material 16 is contained within the retina 12 and is separated from the lens capsule by the vitreous membrane 23. The lens capsule has an anterior portion 24 and a posterior portion 25 which hold a lens. The lens capsule is connected to the ciliary body 27 by zonules 28. The zonules are hairlike members which convey the muscle reactions of the ciliary body to the lens capsule causing it to change its shape to accommodate varying conditions.

Also shown in FIG. 1 is an instrument 29 which is passed through an opening, usually at the limbus. The instrument 29 is intended to represent an ultrasonic or a mechanical instrument such as described in the aforesaid patent. The purpose of showing the instrument is to designate that during a part of the surgical procedure, all of the lens 26 is fragmented and removed by ultrasonic, mechanical or other type of action or by any other type of surgical procedure. Also, in the removal of the lens 26, it is usually necesary to remove the anterior capsule. In some cases, although not absolutely necessary, the posterior capsule is also removed.

Depending upon the surgical procedure used and the condition of the eye at the time of the operation, the zonules may or may not be removed. Removal is accomplished by ultrasonic or mechanical action or by surgical cutting. The zonules also can be weakened by a chemical action, that is by adding a chemical to the eye rather than removal. The zonules may or may not be left, as desired.

Figure 2:
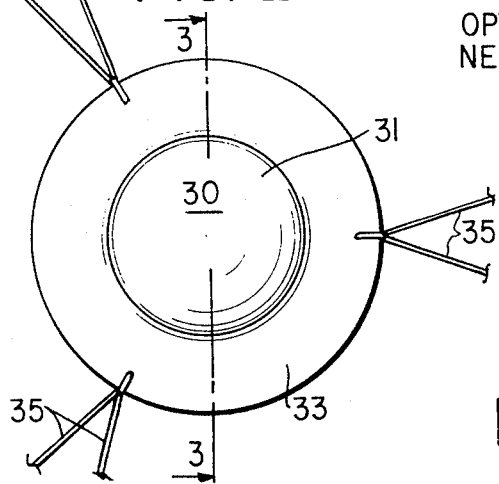
FIG. 2 is a plan view showing a capsule implant in accordance with one embodiment of the invention.
Figure 3:
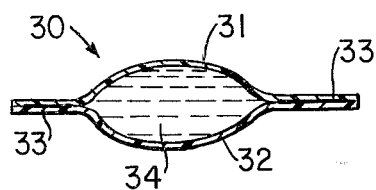
FIG. 3 is a cross-sectional view of the capsule of implant of FIG. 2 along lines 3—3 of FIG. 2.

FIGS. 2 and 3 show one embodiment of the capsule 30. The capsule implant is formed by a suitable plastic material which has deformable and/or elastic properties. One class of materials which is suitable, are the so-called "soft" lens materials used for contact lenses. These are, for example, plastics of the hydrophilic acrylic polymer, e.g. HYDRON, type. The implant capsule 30, which is shown in greatly enlarged form has upper and lower pieces 31 and 32 which are sealed around the edges thereof leaving a lip, or flap, 33 on one or both of the pieces. The sealing is accomplished by heat or ultrasonic sealing or by a waterproof adhesive. The internal part of the capsule 30 is filled with a suitable liquid or semi-viscous material 34, such as, for example a sterile solution or gelatin. Other materials which can be used are plain, or Ringer's saline solution. Each of these materials has a known index of refraction which is combined with that of the plastic material to achieve a desired lens action similar to the eye lens that was removed.

The overall size and shape of the implant capsule 30 approximates or is smaller, than that of the lens capsule which is to be replaced and the overall shape of capsule 30 is that of a double convex lens.

As seen in FIG. 2, the lip 33 is outside of the sealing and active area of the capsule 30. The lip 33 is provided so that there can be attached thereto a plurality of sutures 35. These are attached to the lip 33 by any suitable conventional suturing process either manual or mechanical which takes place either prior to the time that capsule 30 is inserted into the eye or after it is inserted. The sutures also can be attached to lip 33 by an adhesive or by heat or ultrasonic sealing depending upon the type of suture. As many of the sutures 35 can be used as is necessary.

After the lens and the anterior capsule have been removed, with the posterior capsule remaining or not, the capsule 30 is inserted into the eye. This is accomplished by cutting the limbus and making a flap. The limbus is resewn after the operation is completed.

Figure 4:
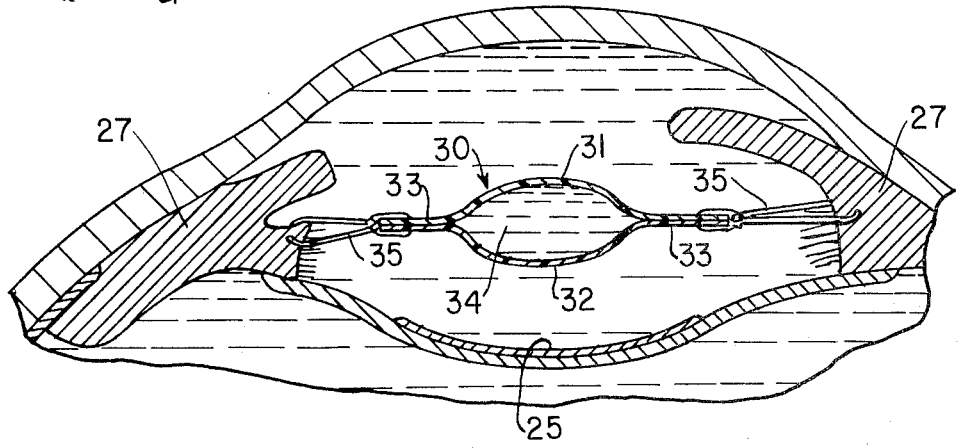
FIG. 4 shows the implantation of the lens of FIGS. 2-3 into the eye.

As shown in FIG. 4, the capsule 30 is sutured to the ciliary body 27. As many sutures can be used as is necessary. In general, the suturing is accomplished all around the periphery of the capsule 30 and it is preferred that at least about 12-16 such sutures can be used spaced more or less equally about the periphery of lip 33.

During the normal operation of the eye, the ciliary bodies act as muscles by a physiologic process to accommodate for different light conditions. In a normal eye the lens focuses light rays upon the retina. To focus light from a distant object, the ciliary muscle relaxes. This pulls on the zonules thereby reducing the antero-posterior diameter of the lens. When in its minimum diameter position, the refractive power of the lens is minimized and parallel rays of light are focused on the retina. To focus rays of light from a near object, the ciliary muscle contracts releasing the tension on the zonules. The elastic lens capsule then shapes the lens into a more spherical shape having greater refractive power.

Since the zonules are preferably removed, they have no control over the capsule 30. The sutures 35 now act effectively as zonules. When the need arises to focus on a distant object, the ciliary body relaxes and tightens the sutures, causing the upper and lower pieces 31, 32 on the material 34 to become flatter. Thus, the lens capsule 30 becomes less refractive. When the need arises to focus on a near object, the contraction of the ciliary body permits the sutures 34 to relax and the capsule to expand to a more nearly spherical shape. Thus, the capsule implant 30 has some of the features and effects of the original eye lens and lens capsule.

Figure 5:
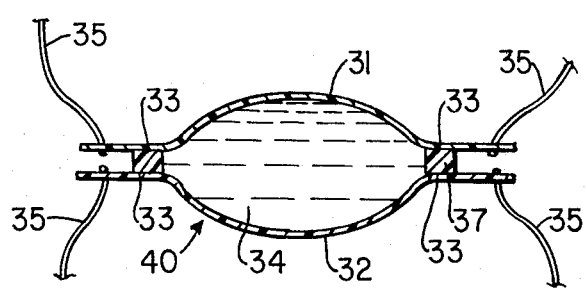
FIG. 5 is a cross-sectional view of a further embodiment of implant capsule.

FIG. 5 is a cross-sectional view of another type of implant capsule 40 which can be used. The implant capsule 40 is also formed of two pieces of plastic 31, 32 material with the flap from each piece beyond the seal 33 being left loose. If desired, a spacer piece 37 can be inserted between the two pieces on the sealing area 33. This provides an arrangement wherein sutures 35 can be independently connected to each of the pieces 31, 32 forming the implant capsule. That is, there will now be a set of upper and lower sutures 35.

In using the implant capsule of FIG. 5, sutures 35 from the lower piece 32 of plastic are sewn to the lower portion of the ciliary muscle. The sutures attached to the upper piece 31 are sewn to the upper portion of ciliary body.

Figure 6:
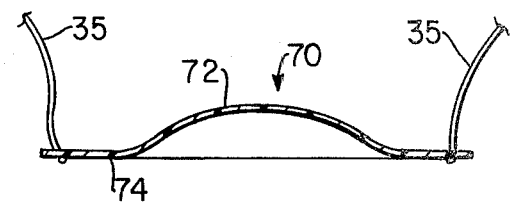
FIGS. 6 and 7 are cross sectional and plan views of a further embodiment of implant.
Figure 7:
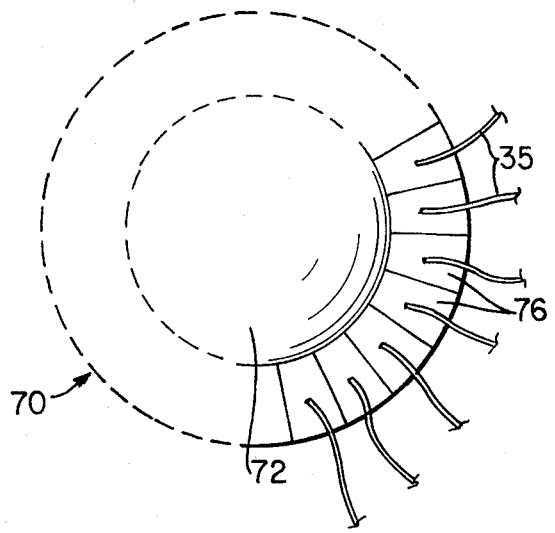

FIGS. 6 and 7 show a further type of implant 70 which does not use a liquid. Here the implant 70 is made of the deformable plastic material, such as of the so-called "soft" lens type. The center portion 72 is formed as a lens and has a diameter somewhat less than the distance between the ciliary body. The contour of portion 72 is made to have a selected optical focus for the light rays, preferably from near objects.

The implant 70 is formed with a surrounding main flap 74 on which is cut a number of sub-flaps 76. A suture 35 is attached to each, or a selected number, of the sub-flaps 76. The other end of each suture is attached to the ciliary body as previously described. The implant 70 is installed and functions in the same manner as the implant 30. The use of the sub-flaps provides a better controlled deformation of the implant by the ciliary body since, effectively, there are a number of control points on the implant 70 which are more independent than if the flap 74 was continuous. Also, circumferential stresses are reduced.

The implant 70 of FIGS. 6-7 can use a continuous flap 74 if this is desired. Also, the implant capsules of FIGS. 2-4 can have their flaps cut to have the respective sub-flaps.

Figure 8:
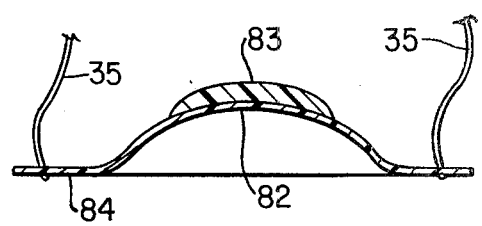
FIG. 8 is a plan view of another type of implant.

FIG. 8 shows a further embodiment of implant 80 which is made along the same lines as implant 70. Here, the flap 84 is continuous, although it could be made with sub-flaps. The major difference is that the central portion of the implant has been provided with a compound lens formed by the lower curved part 82 and the upper, more planar, part 83. Any suitable combination of optical lens characteristics can be used for the parts 82 and 83.

In each of the embodiments of implants, the elasticity of the implant material and/or the liquid filling the capsule, is selected to match the state of the eye. That is, for example, where on old patient is involved whose ciliary muscles are weaker, a material is used which requires less force to make it change its shape than in the case of a younger patient whose ciliary muscles are stronger.

What is claimed is:

1. A method of operating in the eye comprising the steps of:
    removing the lens of the eye and at least the anterior capsule portion,
    inserting a lens implant of a material which is deformable over a portion of its surface into the eye to replace the eye lens, and
    connecting said implant to the ciliary body of the eye so that it can be deformed to change the focal length of the implant as the ciliary body moves.

2. A method as in claim 1 wherein the step of inserting comprises inserting into the removed portion as the lens implant a capsule having a deformable outer wall and a filling of a material which is substantially transparent.

3. A method as in claim 2 wherein the transparent material is at least partly liquid.

4. A method as in claim 1 wherein the step of connecting comprises suturing the implant around its periphery to the ciliary body.

5. A method as in claim 4 wherein the step of suturing comprises providing the implant with a continuous flap around the lens portion of the implant, and attaching the sutures to the implant.

6. A method as in claim 4 wherein the step of suturing comprises providing the implant with a flap around the lens portion of the implant, dividing the flap into a plurality of sub-flaps, and attaching the sutures to selected ones of the sub-flaps.

7. A method as in claim 1 wherein the step of inserting comprises inserting into the removed portion as the lens implant a single piece of deformable material at least a portion of which has optical properties of changing focal length upon deformation.

8. A lens implant for the eye comprising:
    a lens portion of a material which is deformable over at least a portion of its surface to have a variable focal length,
    means attached to said lens portion adapted to hold connecting means to connect the implant to the ciliary body of the eye, and to transmit the forces produced by the ciliary body to said lens portion to cause it to deform.

9. A lens implant as in claim 8 wherein means for holding the connecting means comprises a flap attached to at least a part of said lens portion.

10. A lens implant as in claim 9 wherein said flap is continuous.

11. A lens implant as in claim 9 wherein said flap is divided into a plurality of sub-flaps.

12. A lens implant as in claim 9 further comprising connecting means in the form of a plurality of threads which are attached to said holding means.

13. A lens implant as in claim 8 wherein the lens portion is formed of first and second pieces, means for sealing said pieces at their peripheries and defining a space therebetween, and a transparent material in said space.

14. A lens implant as in claim 13 wherein at least one of said first and second pieces is formed with a peripheral flap which forms said connecting means.

15. A lens implant as in claim 13 wherein both of said pieces are formed with peripheral flaps which are free to move with respect to each other to form said connecting means.

16. A lens implant as in claim 13 wherein said transparent material is at least in part a liquid.

17. A lens implant as in claim 8 wherein the lens portion is of plastic.

18. A lens implant as in claim 17 wherein the lens portion comprises a compound lens.

19. A lens implant as in claim 17 wherein the deformable material is a hydrophilic plastic.

20. A lens implant as in claim 19 wherein the deformable material forms the lens.

21. A lens implant as in claim 8 wherein the lens portion comprises a single piece of deformable material at least a portion of which has optical properties of changing focal length upon deformation.

22. A lens implant as in claim 8 further comprising connecting means in the form of a plurality of threads which are attached to said holding means.

* * * * *